(12) United States Patent
Liu

(10) Patent No.: US 10,613,623 B2
(45) Date of Patent: Apr. 7, 2020

(54) CONTROL METHOD AND EQUIPMENT

(71) Applicant: Beijing Zhigu Rui Tuo Tech Co., Ltd, Beijing (CN)

(72) Inventor: Hao Liu, Beijing (CN)

(73) Assignee: Beijing Zhigu Rui Tuo Tech Co., Ltd, Beijing (CN)

(*) Notice: Subject to any disclaimer, the term of this patent is extended or adjusted under 35 U.S.C. 154(b) by 350 days.

(21) Appl. No.: 15/567,955

(22) PCT Filed: Apr. 20, 2016

(86) PCT No.: PCT/CN2016/079752
§ 371 (c)(1),
(2) Date: Oct. 19, 2017

(87) PCT Pub. No.: WO2016/169478
PCT Pub. Date: Oct. 27, 2016

(65) Prior Publication Data
US 2018/0136717 A1     May 17, 2018

(30) Foreign Application Priority Data
Apr. 20, 2015 (CN) .......................... 2015 1 0187397

(51) Int. Cl.
*G06F 3/01*     (2006.01)
*A61B 5/0496*     (2006.01)
(Continued)

(52) U.S. Cl.
CPC ............ *G06F 3/012* (2013.01); *A61B 5/0496* (2013.01); *A61B 5/6814* (2013.01); *G06F 1/163* (2013.01); *G06F 3/015* (2013.01)

(58) Field of Classification Search
None
See application file for complete search history.

(56) References Cited

U.S. PATENT DOCUMENTS 9,366,862 B2 * 6/2016 Haddick ............ G02B 27/0093
2004/0070729 A1 * 4/2004 Wiebe ...................... G06F 3/012
351/209
(Continued)

FOREIGN PATENT DOCUMENTS

CN     1767873 A     5/2006
CN     101599127     12/2009
(Continued)

OTHER PUBLICATIONS

Chinese Office Action dated Jun. 19, 2018 for Chinese Application No. 201510187397.4, 46 pages (with translation).
(Continued)

*Primary Examiner* — Duane N Taylor, Jr.
(74) *Attorney, Agent, or Firm* — Amin, Turocy & Watson, LLP

(57) ABSTRACT

A control method and equipment are provided, which relate to the field of electronic equipment. A method comprises: acquiring, in response to a head movement executed by a user, electrooculographic information of the user; and executing an operation corresponding to the head movement according to the electrooculographic information and at least one piece of reference information. A control operation according to electrooculographic information is provided, and, for some equipment integrated with an electrooculographic transducer, a corresponding control function can be implemented by multiplexing the electrooculographic information captured by the electrooculographic transducer by using the method, thereby reducing implementation costs.

22 Claims, 5 Drawing Sheets

Equipment 400

Acquiring module 410

Executing module 420

(51) Int. Cl.
*A61B 5/00* (2006.01)
*G06F 1/16* (2006.01)

(56) References Cited

U.S. PATENT DOCUMENTS

| | | | |
|---|---|---|---|
| 2010/0240982 A1* | 9/2010 | Westbrook | A61B 5/087 600/391 |
| 2012/0236031 A1* | 9/2012 | Haddick | G02B 27/0093 345/633 |
| 2014/0330396 A1 | 11/2014 | Chang et al. | |
| 2016/0235323 A1* | 8/2016 | Tadi | A61B 5/7285 |
| 2017/0220109 A1 | 8/2017 | Liu | |

FOREIGN PATENT DOCUMENTS

| | | |
|---|---|---|
| CN | 101711709 | 5/2010 |
| CN | 101890719 A | 11/2010 |
| CN | 102968072 | 3/2013 |
| CN | 103294180 A | 9/2013 |
| CN | 103513770 | 1/2014 |
| CN | 104133549 A | 11/2014 |
| CN | 104182041 A | 12/2014 |
| CN | 104503588 | 4/2015 |
| CN | 104503592 | 4/2015 |
| CN | 104503593 | 4/2015 |
| KR | 20130057166 A | 5/2013 |

OTHER PUBLICATIONS

International Search Report for PCT Application No. PCT/CN2016/079752, dated Jul. 21, 2016, 3 pages.
Zhang Xu, et al., "Exploration on the Feasibility of Building Muscle-Computer Interfaces using Neck and Shoulder Motions", 31st Annual International Conference of the IEEE EMBS, Minneapolis, Minnesota, USA, Sep. 2-6, 2009, 4 pages.

* cited by examiner

CONTROL METHOD AND EQUIPMENT

RELATED APPLICATION

The present application is a U.S. National Stage filing under 35 U.S.C. § 371 of international patent cooperation treaty (PCT) application No. PCT/CN2016/079752, filed Apr. 20, 2016, and entitled "CONTROL METHOD AND EQUIPMENT", which claims the benefit of priority to Chinese Patent Application No. 201510187397.4, filed on Apr. 20, 2015, which applications are hereby incorporated into the present application by reference herein in their respective entireties.

TECHNICAL FIELD

The present application relates to the field of electronic equipment, and, for example, to a control method and equipment.

BACKGROUND

At present, new technologies such as wearable computing, moving computing, and pervasive computing are developing rapidly, which raises new challenges and higher requirements for human-machine interaction technologies and also provides many new opportunities. In this stage, natural and harmonious human-machine interaction methods have been developed for a certain degree, with a major feature of performing multi-channel interaction based on input means such as gestures, voices, handwriting, or tracking, and expressions, and with the objective of enabling an individual to be capable of performing an interactive operation in a natural method such as a movement, a sound, and an expression, in which an ideal "user freedom" that is emphasized in the human-machine interaction exactly lies.

In conventional head movement-based control methods, generally an acceleration transducer, a gyroscope, or the like is provided on a head portion, and a corresponding control operation is then executed according to information such as a speed change and an angle change produced in a process of a head movement.

By the aforementioned method, implementation costs increase because hardware equipment such as an accelerator is added.

SUMMARY

An example objective of the present application is: to provide a control method and equipment, so as to reduce implementation costs.

An aspect of at least one example embodiment of the present application provides a control method, comprising:
acquiring, in response to a head movement executed by a user, electrooculographic information of the user; and
executing an operation corresponding to the head movement according to the electrooculographic information and at least one piece of reference information.

An aspect of at least one example embodiment of the present application provides control equipment, comprising:
an acquiring module, configured to acquire, in response to a head movement executed by a user, electrooculographic information of the user; and
an executing module, configured to execute an operation corresponding to the head movement according to the electrooculographic information and at least one piece of reference information.

By the method and the equipment of the example embodiments of the present application, in response to a head movement executed by a user, electrooculographic information of the user is acquired, and an operation corresponding to the head movement is executed according to the electrooculographic information and at least one piece of reference information. Therefore, a control method for executing a corresponding operation according to electrooculographic information is provided; and for some equipment integrated with an electrooculographic transducer, for example, a smart glass, the electrooculographic information captured by the electrooculographic transducer can be multiplexed by using the method, thereby reducing implementation costs.

DETAILED DESCRIPTION

Specific implementations of the present application are described in further detail below with reference to the accompanying drawings and embodiments. The following embodiments are intended to describe the present application, but not to limit the scope of the present application.

It should be understood by a person skilled in the art that in various embodiments of the present application, the value of the serial number of each step described above does not mean an execution sequence, and the execution sequence of each step should be determined according to the function and internal logic thereof, and should not be any limitation on the implementation procedure of the embodiments of the present application.

Figure 1:
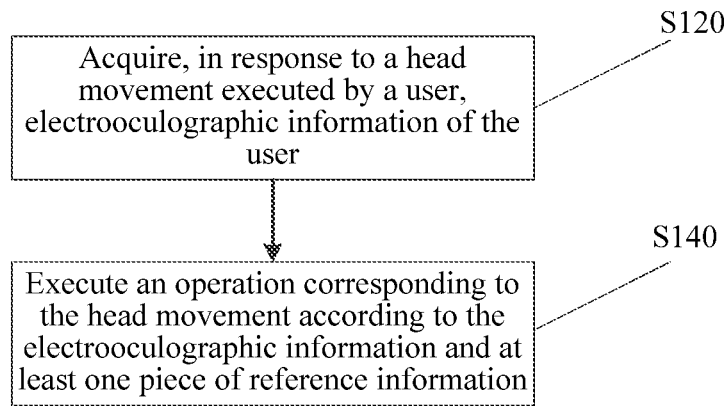
FIG. 1 is a flowchart of a control method of an example embodiment of the present application.

FIG. 1 is a flowchart of the control method of an embodiment of the present application. The method can be implemented on control equipment, for example. As shown in FIG. 1, the method comprises:

S120: Acquire, in response to a head movement executed by a user, electrooculographic information of the user.

S140: Execute an operation corresponding to the head movement according to the electrooculographic information and at least one piece of reference information.

By the method of the embodiments of the present application, in response to a head movement executed by a user, electrooculographic information of the user is acquired, and an operation corresponding to the head movement is executed according to the electrooculographic information and at least one piece of reference information. Therefore, a control method for executing a corresponding operation according to electrooculographic information is provided; and for some equipment integrated with an electrooculographic transducer, for example, a smart glass, a corresponding control function can be implemented by multiplexing the electrooculographic information captured by the electrooculographic transducer by using the method, thereby reducing implementation costs.

Functions of step S120 and step S140 are described in detail below with reference to specific implementations.

S120: Acquire, in response to a head movement executed by a user, electrooculographic information of the user.

The head movement is a movement performed by a head portion of the user, for example, nodding head and shaking head. The electrooculographic information may be left-eye electrooculographic information or right-eye electrooculographic information of the user, which may be acquired by using an electrooculographic transducer on the smart glass.

S140: Execute an operation corresponding to the head movement according to the electrooculographic information and at least one piece of reference information.

In an implementation, step S140 may comprise:

S141: Determine related information of the head movement according to the electrooculographic information and the at least one piece of reference information.

S142: Execute the operation according to the related information.

In an implementation, the related information of the head movement may comprise a type of the head movement, for example, nodding head or shaking head. Correspondingly, step S141 may comprise:

S1411: Determine a type of the head movement according to the electrooculographic information and the at least one piece of reference information.

In an implementation, step S1411 may comprise:

S14111a: Determine a target waveform in the electrooculographic information.

S14112a: Determine the type of the head movement according to the target waveform and at least one reference waveform.

In step S14111a, the target waveform is a waveform, that is corresponding to the head movement, among waveforms of the electrooculographic information, and is obviously different from a waveform of the electrooculographic information captured when the head portion does not execute any movement.

Figure 2:
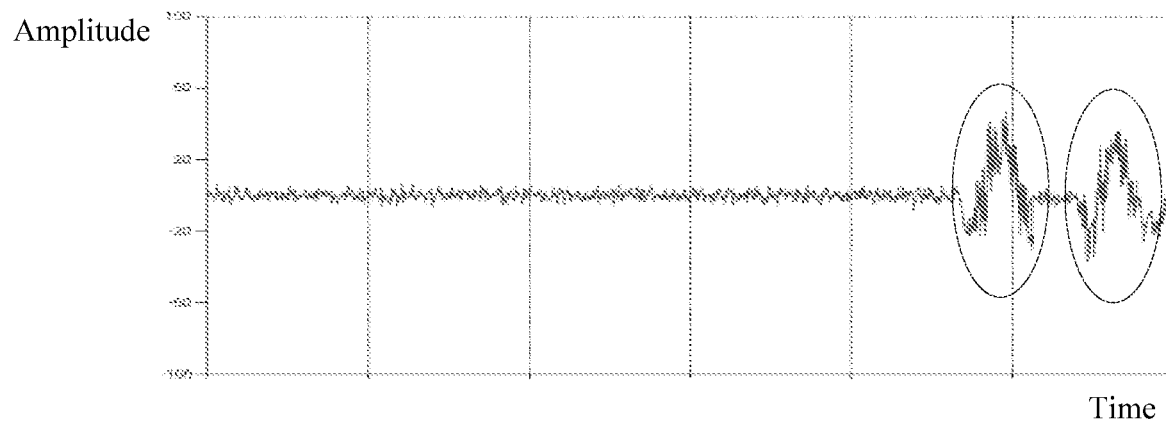
FIG. 2 is a schematic waveform diagram of electrooculographic information corresponding to a nodding head movement in an example embodiment of the present application.

By using the type of the head movement being a nodding head movement as an example, the obtained waveforms of the electrooculographic information are shown in FIG. 2. The waveforms in the ellipses are waveforms when the head portion of the user executes a nodding head movement, and the waveforms outside the ellipses are waveforms when the head portion of the user does not execute any movement. It can be known that the waveforms in the ellipses are obviously different from the waveforms outside the ellipses in FIG. 2. Specifically, amplitude of oscillation of the waveforms in the ellipses is obviously greater than amplitude of oscillation of the waveforms outside the ellipses. On the basis of the above, the target waveform can be extracted from the electrooculographic information, i.e., it can be determined that the waveforms in the ellipses are the target waveform.

Figure 3:
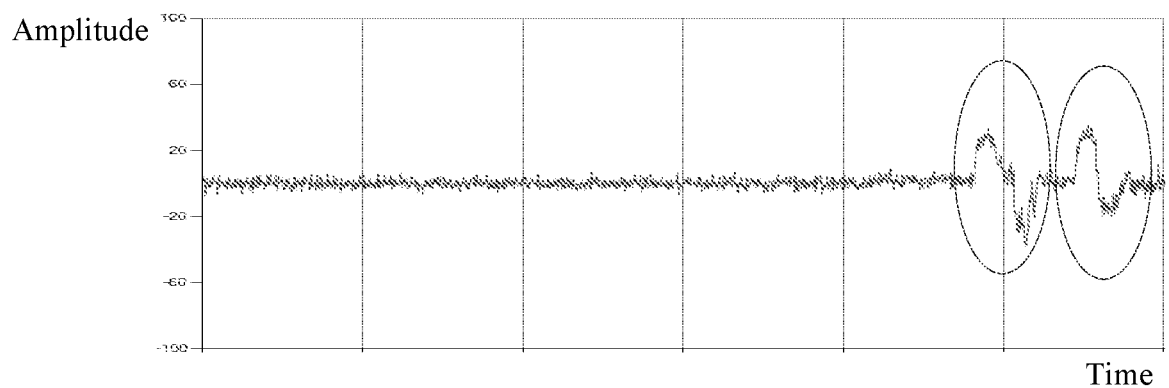
FIG. 3 is a schematic waveform diagram of electrooculographic information corresponding to a shaking head movement in an example embodiment of the present application.

Similarly, FIG. 3 illustrates waveforms of the electrooculographic information obtained when the type of the head movement is shaking head. The waveforms in the ellipses are waveforms when the head portion of the user executes a shaking head movement, and the waveforms outside the ellipses are waveforms when the head portion of the user does not execute any movement. It can be known that in FIG. 3, amplitude of oscillation of the waveforms in the ellipses is also obviously greater than amplitude of oscillation of the waveforms outside the ellipses. On the basis of the above, it can be determined that the waveforms in the ellipses are the target waveform.

In step S14112a, the reference waveform may be a waveform that is obtained by pretraining and is corresponding to a corresponding head movement. For example, in a training stage, a user is asked to execute different types of head movements, separately, and corresponding waveforms are acquired accordingly and used as the reference waveforms. For example, at a training stage, a user is asked to execute a nodding head movement, and the waveforms in the ellipses in FIG. 2 are accordingly acquired as reference waveforms corresponding to the nodding head movement.

In a situation in which a quantity of the at least one reference waveform is small, that is, a few of types of the head movements are provided, whether the target waveform comprises the at least one reference waveform is determined by using a method of image identification, for example. If the target waveform comprises the at least one reference waveform, the type of the head movement is determined as a type corresponding to the comprised reference waveform. By using FIG. 2 and FIG. 3 for example, it can be known that there is an obvious difference between the target waveform in FIG. 2 and the target waveform in FIG. 3. For example, the trend of the target waveform in FIG. 2 is first fall then rise and the trend of the target waveform in FIG. 3 is first rise then fall. On the basis of the aforementioned difference, different reference waveforms corresponding to the target waveform can be determined, that is, the target waveform can be recognized.

In a situation in which a quantity of the at least one reference waveform is relatively large, a possibility of mixing different reference waveforms increases. To avoid recognition error, in an implementation, step S14112a may comprise:

S14112a': Perform cross-correlation computation on the target waveform and the at least one reference waveform, separately, and determine a type of the head movement according to a computed result.

Specifically, cross-correlation computation is performed on the target waveform and the at least one reference waveform, separately, to obtain a computed result corresponding to each reference waveform, and a type corresponding to a reference waveform having a highest value in the computed result (that is, a reference waveform having a highest correlation with the target waveform) is then selected as the type of the head movement. For example, it is assumed that the at least one reference waveform comprises a first reference waveform corresponding to nodding head and a second reference waveform corresponding to shaking head, the cross-correlation computation is performed on the first reference waveform and the target waveform to obtain a first result, and the cross-correlation computation is performed on the second reference waveform and the target waveform to obtain a second result; and if a value of the first result is higher than a value of the second result, it can be determined that the type of the head movement is nodding head.

In another implementation, step S1411 may comprise:

S14111b: Determine a target signal characteristic in the electrooculographic information.

S14112b: Determine the type of the head movement according to the target signal characteristic and at least one reference signal characteristic.

In step S14111b, the target signal characteristic may be understood as the signal characteristic of the target waveform in the previous implementation, and the target signal characteristic may be correlated with at least one item of amplitude, phase, and spectrum of the target waveform. Specifically, the target signal characteristic may comprise: at least one item of fingerprint, average value, and difference; the fingerprint may be composed of at least one item of the amplitude, the phase, and the spectrum of the target waveform; the average value may be an average value of at least one item of the amplitude, the phase, and the spectrum of the target waveform; and the difference may be a difference of at least one item of the amplitude, the phase, and the spectrum of the target waveform. Certainly, it should be understood by a person skilled in the art that the target signal characteristic may be directly determined according to data of the electrooculographic information, not necessarily according to the target waveform.

In step S14112b, the reference signal characteristic may be a signal characteristic that is obtained by pretraining and is corresponding to a corresponding head movement. For example, in a training stage, a user is asked to execute different types of head movements, separately, and signal characteristics of the corresponding electrooculographic information are acquired accordingly and used as the reference signal characteristics. For example, at a training stage, a user is asked to execute a nodding head movement, and the waveforms in the ellipses in FIG. 2 are accordingly acquired as reference signal characteristics corresponding to the nodding head movement.

In step S14112b, whether the target signal characteristic comprises the at least one reference signal characteristic may be determined by using a method of comparing signal characteristics, for example, and if the target signal characteristic comprises the at least one reference signal characteristic, the type of the head movement is determined as a type corresponding to the comprised reference signal characteristic.

The type of the head movement may represent a different operation command, for example, the nodding head represents confirmation and the shaking head represents canceling. Meanwhile, for a different type of head movement, to execute the different type of head movement for a different number of times may also represent a different operation command. For example, nodding head once represents selected and nodding head twice successively represents opening. Therefore, in an implementation, the head movement comprises a first type head movement; and the at least one piece of reference information comprises first reference information corresponding to the first type head movement.

Correspondingly, step S141 may further comprise:

S1412: Determine the number of the first type head movements according to the electrooculographic information and the first reference information.

In an implementation, step S1412 may comprise:

S14121a: Determine a target waveform in the electrooculographic information.

S14122a: Determine the number of the first type head movements according to a quantity of the first reference waveforms comprised in the target waveform.

The implementation principles of step S14121a are the same as the implementation principles of step S14111a, which are not described herein again.

In step S14122a, the quantity of the first reference waveforms comprised in the target waveform is corresponding to the number of the first type head movements. It is assumed that the first type head movement is nodding head, and the first reference waveform is a reference waveform corresponding to the nodding head. By using FIG. 2 as an example, it can be known that the target waveform comprises two of such the first reference waveforms, and it can be therefore determined that the user conducts the nodding head movement twice. Similarly, the electrooculographic information shown in FIG. 3 represents that the user conducts the shaking head movement twice.

In another implementation, step S1412 may comprise:

S14121b: Determine a target signal characteristic in the electrooculographic information.

S14122b: Determine the number of the first type head movements according to a quantity of the first reference signal characteristics comprised in the target signal characteristic.

The implementation principles of step S14121b are the same as the implementation principles of step S14111b, which are not described herein again.

In step S14122b, the quantity of the first reference signal characteristic comprised in the target signal characteristic is corresponding to the number of the first type head movements. It is still assumed that the first type head movement is nodding head and the first reference signal characteristic is variable data of an amplitude value corresponding to the nodding head (for example, the amplitude value first falls below −20, then rises to exceed 20, and again falls below −20). By using FIG. 2 as an example, it can be known that the target signal characteristic in the electrooculographic information comprises two of such the first reference signal characteristics, and therefore it can be determined that the user conducts the nodding head movement twice. Certainly, it should be understood by a person skilled in the art that it is not a must to obtain the waveform curve shown in FIG. 2 in the step. Similarly, the electrooculographic information shown in FIG. 3 represents that the user conducts the shaking head movement twice.

In addition, the head movement may probably comprise other types of head movements, for example, a second type head movement. Alternatively, the head movement may simultaneously comprise a plurality of types of head movements, for example, the head movement simultaneously comprises a first type head movement and a second type head movement. The number of head movements for each type can be implemented separately according to the aforementioned implementation principles.

In step S142: Execute the operation according to the related information.

The execution operation may comprise an operation, for example, switch mode, input content, prompt user, and match equipment.

For example, in a process in which a user wears a smart glass, a head movement of the user is monitored, and if the user nods head once, a current object is selected, for example, an application icon displayed currently is selected;

if the user nods head twice successively, a current object is opened directly; and if the user shakes head, a next object is switched to.

In addition, it should be noted that to facilitate description of the principles of the method, step S140 in the aforementioned implementations essentially implements the aforementioned control method according to a first correspondence between the at least one piece of reference information and the related information of the head movement and a second correspondence between the related information and the operation.

It should be understood by a person skilled in the art that it is not a must to determine the first correspondence in step S140, because the control method can be implemented according to a third correspondence between the at least one piece of reference information and the operation only. That is, in another implementation, there is readily a correspondence between the at least one piece of reference information and the operation. Therefore, according to the electrooculographic information and the at least one piece of reference information, the operation can be readily determined and executed. For example, it is assumed that the at least one piece of reference information comprises target reference information corresponding to a turn-off command. In a situation when a user executes a head movement to trigger electrooculographic information and the electrooculographic information matches the target reference information, corresponding electronic equipment can be controlled to be turned off directly.

Besides, an embodiment of the present application further provides a computer-readable medium, comprising computer-readable instructions that perform, and when being executed, the following operations: operations of executing steps S120 and S140 of the method in the implementation shown in FIG. 1.

In view of the above, by the method of the embodiments of the present application, a corresponding operation is executed according to electrooculographic information triggered by a head movement of a user, and it is convenient for the user to control corresponding electronic equipment through a head movement in a premise of not increasing implementation costs.

Figure 4:
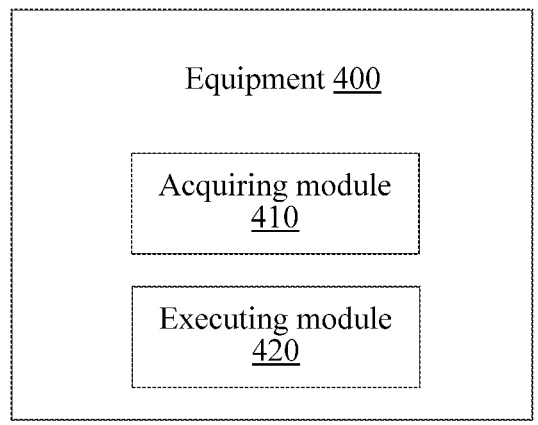
FIG. 4 is a module chart of the control equipment in another example embodiment of the present application.

FIG. 4 is a schematic diagram of module structure of the control equipment of an embodiment of the present application. The equipment may be independent control equipment, and certainly can also be configured as a functional module to be integrated in wearable equipment such as a smart glass. Referring to FIG. 4, the equipment 400 may comprise:

an acquiring module 410, configured to acquire, in response to a head movement executed by a user, electrooculographic information of the user; and an executing module 420, configured to execute an operation corresponding to the head movement according to the electrooculographic information and at least one piece of reference information.

By the equipment of the embodiments of the present application, in response to a head movement executed by a user, electrooculographic information of the user is acquired, and an operation corresponding to the head movement is executed according to the electrooculographic information and at least one piece of reference information. Therefore, a control method for executing a corresponding operation according to electrooculographic information is provided; and for some equipment integrated with an electrooculographic transducer, for example, a smart glass, control of the equipment or other equipment can be implemented by multiplexing the electrooculographic information captured by the electrooculographic transducer, thereby reducing implementation costs.

Functions of the acquiring module 410 and the executing module 420 are described in detail in combination with specific implementations below.

The acquiring module 410 is configured to acquire, in response to a head movement executed by a user, electrooculographic information of the user.

The head movement is a movement performed by a head portion of the user, for example, nodding head and shaking head. The electrooculographic information may be left-eye electrooculographic information or right-eye electrooculographic information of the user, which may be acquired by using an electrooculographic transducer on the smart glass.

The executing module 420 is configured to execute an operation corresponding to the head movement according to the electrooculographic information and at least one piece of reference information.

Figure 5:
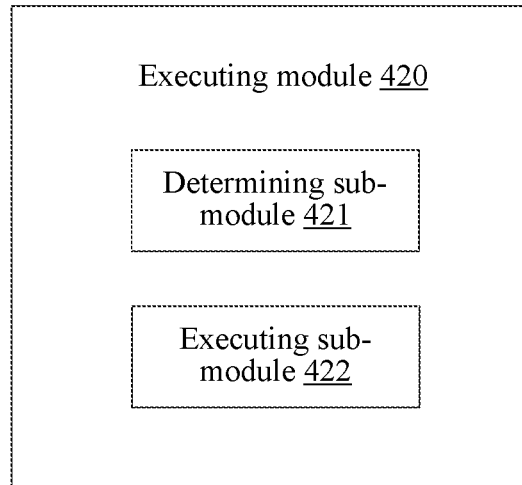
FIG. 5 is a module chart of the executing module in an example embodiment of the present application.

Referring to FIG. 5, in an implementation, the executing module 420 may comprise:

a determining sub-module 421, configured to determine related information of the head movement according to the electrooculographic information and the at least one piece of reference information; and an executing sub-module 422, configured to execute the operation according to the related information.

Figure 6:
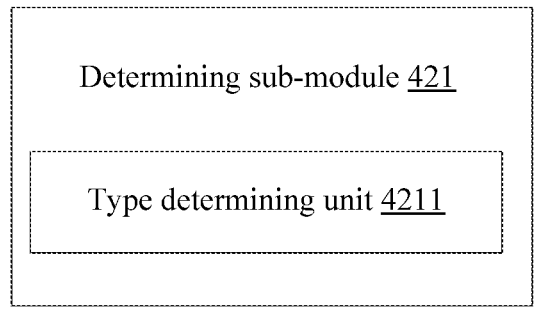
FIG. 6 is a module chart of the determining sub-module in an example embodiment of the present application.

In an implementation, the related information of the head movement may comprise a type of the head movement, for example, nodding head or shaking head. Correspondingly, referring to FIG. 6, the determining sub-module 421 may comprise:

a type determining unit 4211, configured to determine a type of the head movement according to the electrooculographic information and the at least one piece of reference information.

Figure 7:
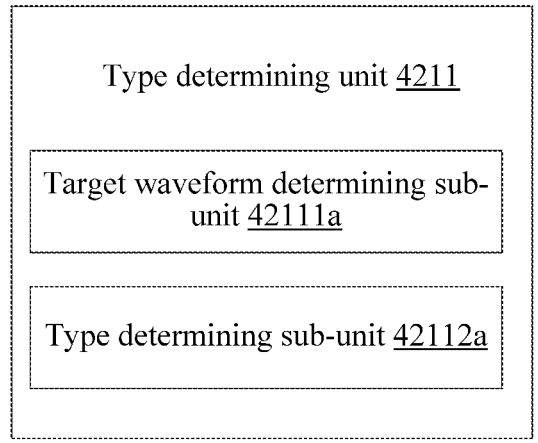
FIG. 7 is a module chart of the type determining unit in an example embodiment of the present application.

In an implementation, referring to FIG. 7, the type determining unit 4211 may comprise:

a target waveform determining sub-unit 42111a, configured to determine a target waveform in the electrooculographic information; and a type determining sub-unit 42112a, configured to determine a type of the head movement according to the target waveform and at least one reference waveform.

In the target waveform determining sub-unit 42111a, the target waveform is a waveform, which is corresponding to the head movement, among waveforms of the electrooculographic information, and is obviously different from a waveform of the electrooculographic information captured when the head portion does not execute any movement.

By using the type of the head movement being a nodding head movement as an example, the obtained waveforms of the electrooculographic information are shown in FIG. 2. The waveforms in the ellipses are waveforms when the head portion of the user executes a nodding head movement, and the waveforms outside the ellipses are waveforms when the head portion of the user does not execute any movement. It can be known that the waveforms in the ellipses are obviously different from the waveforms outside the ellipses in FIG. 2. Specifically, amplitude of oscillation of the waveforms in the ellipses is obviously greater than amplitude of oscillation of the waveforms outside the ellipses. On the basis of the above, the target waveform can be extracted from the electrooculographic information, i.e., it can be determined that the waveforms in the ellipses are the target waveform.

Similarly, FIG. 3 illustrates waveforms of the electrooculographic information obtained when the type of the head movement is shaking head. The waveforms in the ellipses are waveforms when the head portion of the user executes a shaking head movement, and the waveforms outside the ellipses are waveforms when the head portion of the user does not execute any movement. It can be known that in FIG. 3, amplitude of oscillation of the waveforms in the ellipses is also obviously greater than amplitude of oscillation of the waveforms outside the ellipses. On the basis of the above, it can be determined that the waveforms in the ellipses are the target waveform.

In the type determining sub-unit 42112a, the reference waveform may be a waveform that is obtained by pretraining and is corresponding to a corresponding head movement. For example, in a training stage, a user is asked to execute different types of head movements, separately, and corresponding waveforms are acquired accordingly and used as the reference waveforms. For example, at a training stage, a user is asked to execute a nodding head movement, and the waveforms in the ellipses in FIG. 2 are accordingly acquired as reference waveforms corresponding to the nodding head movement.

In a situation in which a quantity of the at least one reference waveform is small, that is, a few of types of the head movements are provided, whether the target waveform comprises the at least one reference waveform is determined by using a method of image identification, for example. If the target waveform comprises the at least one reference waveform, the type of the head movement is determined as a type corresponding to the comprised reference waveform. By using FIG. 2 and FIG. 3 for example, it can be known that there is an obvious difference between the target waveform in FIG. 2 and the target waveform in FIG. 3. For example, the trend of the target waveform in FIG. 2 is first fall then rise and the trend of the target waveform in FIG. 3 is first rise then fall. On the basis of the aforementioned difference, different reference waveforms corresponding to the target waveform can be determined, that is, the target waveform can be recognized.

In a situation in which the quantity of the at least one reference waveform is relatively large, a possibility of mixing different reference waveforms increases. To avoid recognition error, in an implementation, the type determining sub-unit 42112a is configured to perform cross-correlation computation on the target waveform and the at least one reference waveform, separately, and determine the type of the head movement according to a computed result.

Specifically, the type determining sub-unit 42112a performs cross-correlation computation on the target waveform and the at least one reference waveform, separately, to obtain a computed result corresponding to each reference waveform, and then determines a type corresponding to a reference waveform having a highest value in the computed result (that is, a reference waveform having a highest correlation with the target waveform) as the type of the head movement. For example, it is assumed that the at least one reference waveform comprises a first reference waveform corresponding to nodding head and a second reference waveform corresponding to shaking head, the cross-correlation computation is performed on the first reference waveform and the target waveform to obtain a first result, and the cross-correlation computation is performed on the second reference waveform and the target waveform to obtain a second result; and if a value of the first result is higher than a value of the second result, it can be determined that the type of the head movement is nodding head.

Figure 8:
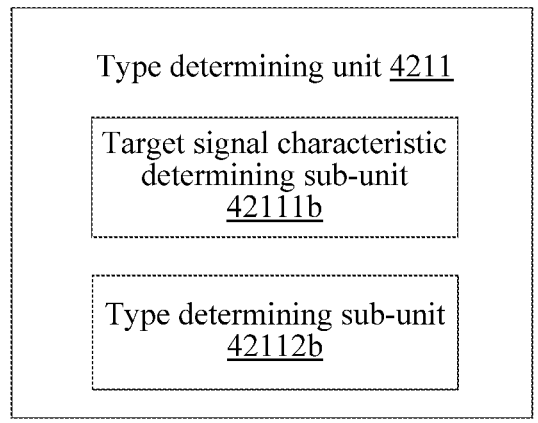
FIG. 8 is a module chart of the type determining unit in another example embodiment of the present application.

In another implementation, referring to FIG. 8, the type determining unit 4211 may comprise:

a target signal characteristic determining sub-unit 42111b, configured to determine a target signal characteristic in the electrooculographic information; and a type determining sub-unit 42112b, configured to determine a type of the head movement according to the target signal characteristic and at least one reference signal characteristic.

In the target signal characteristic determining sub-unit 42111b, the target signal characteristic may be understood as a signal characteristic of the target waveform in the previous implementation, and the target signal characteristic may be correlated with at least one item of amplitude, phase, and spectrum of the target waveform. Specifically, the target signal characteristic may comprise: at least one item of fingerprint, average value, and difference; the fingerprint may be composed of at least one item of the amplitude, the phase, and the spectrum of the target waveform; the average value may be an average value of at least one item of the amplitude, the phase, and the spectrum of the target waveform; and the difference may be a difference of at least one item of the amplitude, the phase, and the spectrum of the target waveform. Certainly, it should be understood by a person skilled in the art that the target signal characteristic may be directly determined according to data of the electrooculographic information, not necessarily according to the target waveform.

In the type determining sub-unit 42112b, the reference signal characteristic may be a signal characteristic that is obtained by pretraining and is corresponding to a corresponding head movement. For example, in a training stage, a user is asked to execute different types of head movements, separately, and signal characteristics of the corresponding electrooculographic information are acquired accordingly and used as the reference signal characteristics. For example, at a training stage, a user is asked to execute a nodding head movement, and the waveforms in the ellipses in FIG. 2 are accordingly acquired as reference signal characteristics corresponding to the nodding head movement.

In the type determining sub-unit 42112b, whether the target signal characteristic comprises the at least one reference signal characteristic may be determined by using a method of comparing signal characteristics, for example, and if the target signal characteristic comprises the at least one reference signal characteristic, the type of the head movement is determined as a type corresponding to the comprised reference signal characteristic.

Figure 9:
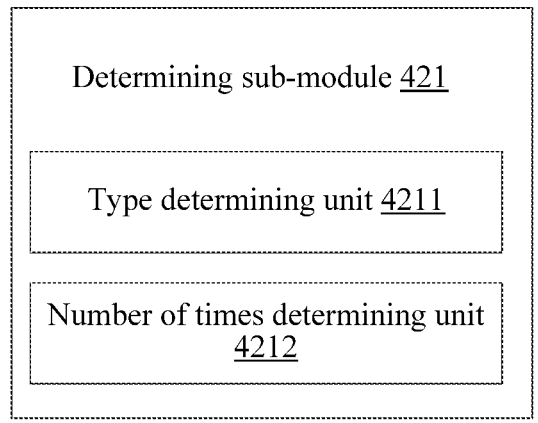
FIG. 9 is a module chart of the determining sub-module in another example embodiment of the present application.

The type of the head movement may represent a different operation command, for example, the nodding head represents confirmation and the shaking head represents canceling. Meanwhile, for a different type of head movement, to execute the different type of head movement for a different number of times may also represent a different operation command. For example, nodding head once represents selected and nodding head twice successively represents opening. Therefore, in an implementation, the head movement comprises a first type head movement; and the at least one piece of reference information comprises first reference information corresponding to the first type head movement. Correspondingly, referring to FIG. 9, the determining sub-module 421 further comprises:

a number of times determining unit 4212, configured to determine the number of the first type head movements according to the electrooculographic information and the first reference information.

Figure 10:
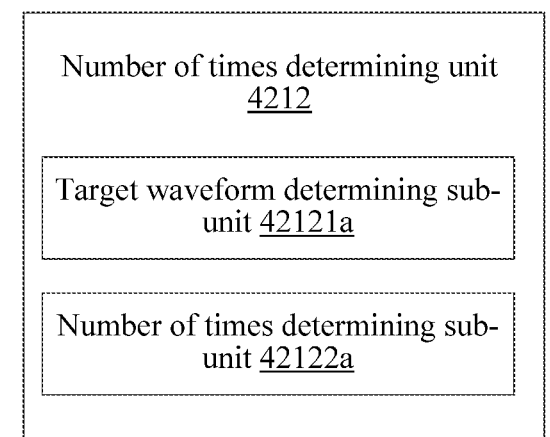
FIG. 10 is a module chart of the number of times determining unit in an example embodiment of the present application.

In an implementation, referring to FIG. 10, the number of times determining unit 4212 may comprise:

a target waveform determining sub-unit 42121a, configured to determine a target waveform in the electrooculographic information; and a number of times determining sub-unit 42122a, configured to determine the number of the first type head movements according to a quantity of first reference waveforms comprised in the target waveform.

The implementation principles of the target waveform determining sub-unit 42121a are the same as the implementation principles of the target waveform determining sub-unit 42111a, which are not described herein again.

In the number of times determining sub-unit 42122a, the quantity of the first reference waveforms comprised in the target waveform is corresponding to the number of the first type head movements. It is assumed that the first type head movement is nodding head, and the first reference waveform is a reference waveform corresponding to the nodding head. By using FIG. 2 as an example, it can be known that the target waveform comprises two of such the first reference waveforms, and it can be therefore determined that the user conducts the nodding head movement twice. Similarly, the electrooculographic information shown in FIG. 3 represents that the user conducts the shaking head movement twice.

Figure 11:
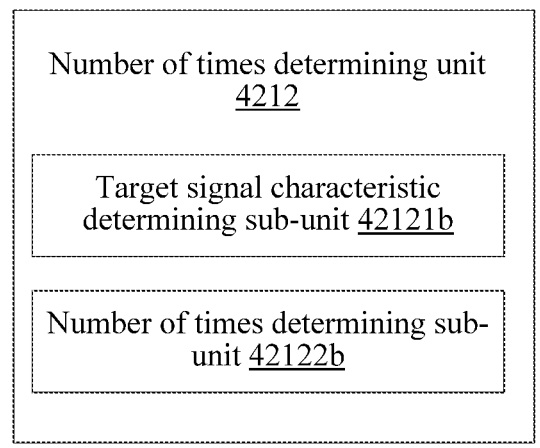
FIG. 11 is a module chart of the number of times determining unit in another example embodiment of the present application.

In another implementation, referring to FIG. 11, the number of times determining unit 4212 may comprise:

a target signal characteristic determining sub-unit 42121b, configured to determine a target signal characteristic in the electrooculographic information; and a number of times determining sub-unit 42122b, configured to determine the number of the first type head movements according to a quantity of first reference signal characteristics comprised in the target signal characteristic.

The implementation principles of the target signal characteristic determining sub-unit 42121b are the same as the implementation principles of the target signal characteristic determining sub-unit 42111b, which are not described herein again.

In the number of times determining sub-unit 42122b, the quantity of the first reference signal characteristics comprised in the target signal characteristic is corresponding to the number of the first type head movements. It is still assumed that the first type head movement is nodding head and the first reference signal characteristic is variable data of an amplitude value corresponding to the nodding head (for example, the amplitude value first falls below −20, then rises to exceed 20, and again falls below −20). By using FIG. 2 as an example, it can be known that the target signal characteristic in the electrooculographic information comprises two of such the first reference signal characteristics, and therefore it can be determined that the user conducts the nodding head movement twice. Certainly, it should be understood by a person skilled in the art that it is not a must to obtain the waveform curve shown in FIG. 2 in the step. Similarly, the electrooculographic information shown in FIG. 3 represents that the user conducts the shaking head movement twice.

In addition, the head movement may probably comprise other types of head movements, for example, a second type head movement. Alternatively, the head movement may simultaneously comprise a plurality of types of head movements, for example, the head movement simultaneously comprises a first type head movement and a second type head movement. The number of head movements for each type can be implemented separately according to the aforementioned implementation principles.

The executing sub-module 422 is configured to execute the operation according to the related information.

The execution operation may comprise an operation, for example, switch mode, input content, prompt user, and match equipment.

For example, in a process in which a user wears a smart glass, a head movement of the user is monitored, and if the user nods head once, a current object is selected, for example, an application icon displayed currently is selected; if the user nods head twice successively, a current object is opened directly; and if the user shakes head, a next object is switched to.

In view of the above, by the equipment of the embodiments of the present application, a corresponding operation is executed according to electrooculographic information triggered by a head movement, and it is convenient for a user to control corresponding electronic equipment through a head movement in a premise of not increasing implementation costs.

An application scenario of the information processing method and the equipment of the embodiments of the present application may be as follows: a user wears a smart glass, the smart glass initially enters a level-one menu, and an electrooculographic transducer on the smart glass acquires electrooculographic information of the user; the user executes a shaking head movement to trigger first electrooculographic information, and the smart glass controls, according to the first electrooculographic information, options on the level-one menu to switch in a glass display window according to a predetermined sequence; and when an application that the user wants to open is switched to, the user executes a nodding head movement to trigger second electrooculographic information, the application is selected, the user then executes the nodding head movement twice successively to trigger third electrooculographic information, and the application is opened.

Figure 12:
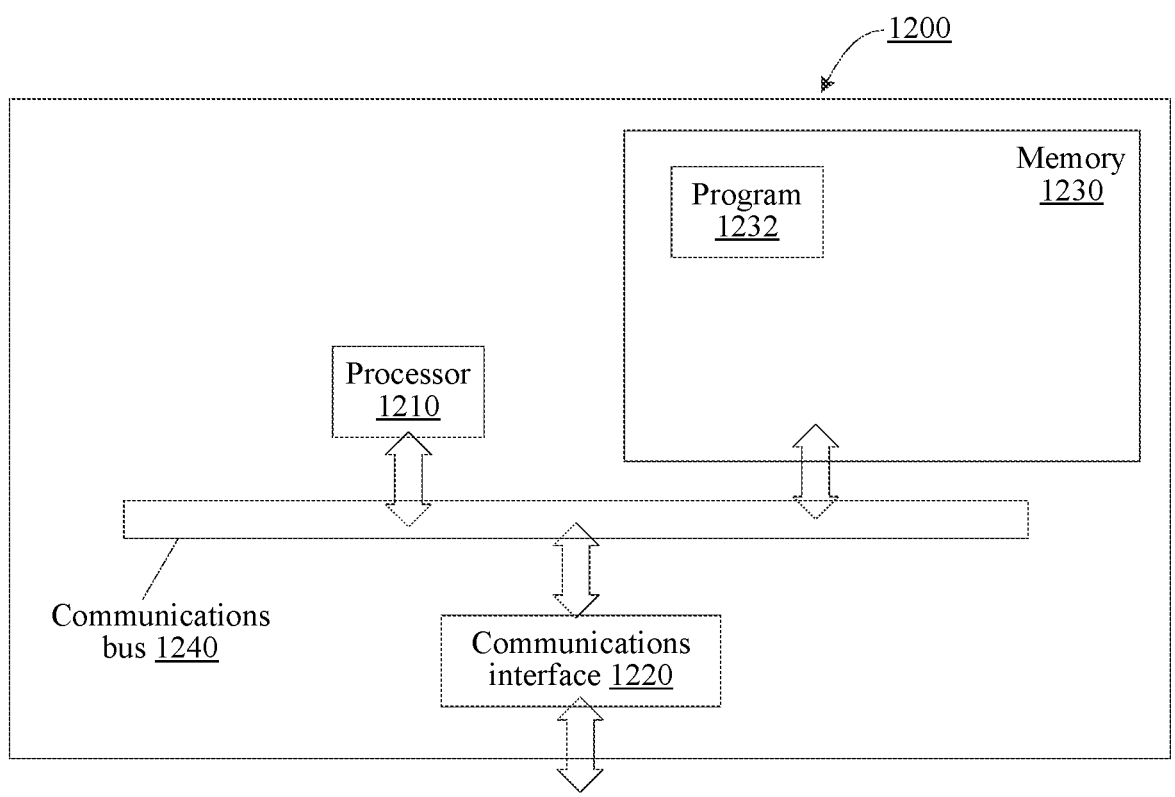
FIG. 12 is a schematic diagram of a hardware structure of the control equipment in an example embodiment of the present application.

The hardware structure of the control equipment of another implementation of the present application is shown in FIG. 12. The specific embodiments of the present application do not specifically limit the implementations of the control equipment. Referring to FIG. 12, the equipment 1200 may comprise:

a processor 1210, a communications interface 1220, a memory 1230, and a communications bus 1240. Where:

The processor 1210, the communications interface 1220, and the memory 1230 communicate with each other by using the communications bus 1240.

The communications interface 1220 is configured to communicate with other network elements.

The processor 1210 is configured to execute a program 1232, and specifically can perform relevant steps in the aforementioned embodiments of the method shown in FIG. 1.

Specifically, the program 1232 may comprise a program code, where the program code comprises a computer operation instruction.

The processor 1210 may be a Central Processing Unit (CPU), an Application Specific Integrated Circuit (ASIC), or one or more integrated circuits configured to implement the embodiments of the present application.

The memory 1230 is configured to store the program 1232. The memory 1230 may comprise a high speed RAM memory, and may further comprise a non-volatile memory such as at least one magnetic disk memory. The program 1232 specifically may execute the following steps:

acquiring, in response to a head movement executed by a user, electrooculographic information of the user; and executing an operation corresponding to the head movement according to the electrooculographic information and at least one piece of reference information.

For the specific implementation of the steps in the program 1232, refer to the corresponding descriptions of corresponding steps or modules in the aforementioned embodiments, which are not described herein again. It may be clearly understood by a person skilled in the art that, for the purpose of convenient and brief description, reference may be made to the description of corresponding processes in the foregoing method embodiments for detailed working processes of the foregoing devices and modules, and details are not described herein again.

A person of ordinary skill in the art may be aware that, in combination with the examples described in the embodiments disclosed in this specification, units and steps of the method may be implemented by electronic hardware or a combination of computer software and electronic hardware. Whether the functions are performed by hardware or software depends on particular applications and design constraint conditions of the technical solutions. A person skilled in the art may use different methods to implement the described functions for each particular application, but it should not be considered that the implementation goes beyond the scope of the present application.

When the functions are implemented in a form of a software functional unit and sold or used as an independent product, the functions may be stored in a computer-readable storage medium. Based on such an understanding, the technical solutions of the present application essentially, or the part contributing to the existing art, or all or a part of the technical solutions may be implemented in the form of a software product. The software product is stored in a storage medium and comprises several instructions for instructing a computer device (which may be a personal computer, a controller, or a network device) or a processor to perform all or a part of the steps of the methods in the embodiments of the present application. The aforementioned storage medium comprises: any medium that can store a program code, such as a USB flash drive, a removable hard disk, a read-only memory (ROM), a random access memory (RAM), a magnetic disk, or an optical disc.

The above implementations are only used to describe the present application, rather than limit the present application; various alterations and variants can be made by those of ordinary skill in the art without departing from the spirit and scope of the present application, so all equivalent technical solutions also belong to the scope of the present application, and the scope of patent protection of the present application should be defined by claims.

What is claimed is:

1. A method, comprising:
in response to a head movement determined to have been executed by a user, acquiring, by a wearable smart glass device comprising a processor, electrooculographic information of the user; and
executing, by the wearable smart glass device, an operation corresponding to the head movement according to the electrooculographic information and at least one piece of reference information.

2. The method of claim 1, wherein the executing the operation comprises:
determining related information of the head movement according to the electrooculographic information and the at least one piece of reference information; and
executing the operation according to the related information.

3. The method of claim 2, wherein the determining the related information comprises:
determining a type of the head movement according to the electrooculographic information and the at least one piece of reference information.

4. The method of claim 3, wherein the type of the head movement comprises: at least one of a nodding head or a shaking head.

5. The method of claim 3, wherein the determining the type of the head movement comprises:
determining a target waveform in the electrooculographic information; and
determining the type of the head movement according to the target waveform and at least one reference waveform.

6. The method of claim 5, wherein the determining the type of the head movement according to the target waveform and at least one reference waveform comprises:
performing a cross-correlation between the target waveform and the at least one reference waveform, and determining the type of the head movement according to a computed result of the cross-correlation.

7. The method of claim 3, wherein the determining the type of the head movement comprises:
determining a target signal characteristic in the electrooculographic information; and
determining the type of the head movement according to the target signal characteristic and at least one reference signal characteristic.

8. The method of claim 3, wherein the head movement comprises a first type head movement,
wherein the at least one piece of reference information comprises first reference information corresponding to the first type head movement, and
wherein the determining related information of the head movement according to the electrooculographic information and the at least one piece of reference information further comprises:
determining a number of the first type head movements according to the electrooculographic information and the first reference information.

9. The method of claim 8, wherein the determining the number of the first type head movements according to the electrooculographic information and the first reference information comprises:
determining a target waveform in the electrooculographic information; and
determining the number of the first type head movements according to a quantity of first reference waveforms comprised in the target waveform.

10. The method of claim 8, wherein the determining the number of the first type head movements according to the electrooculographic information and the first reference information comprises:
determining a target signal characteristic in the electrooculographic information; and
determining the number of the first type head movements according to a quantity of first reference signal characteristics comprised in the target signal characteristic.

11. A wearable smart glass device, comprising:
a memory that stores executable modules; and
a processor, coupled to the memory, that executes or facilitates execution of the executable modules, the executable modules comprising:
an acquiring module configured to acquire, in response to a head movement performed by a user, electrooculographic information of the user; and an executing module configured to execute an operation corresponding to the head movement according to the electrooculographic information and a piece of reference information.

12. The wearable smart glass device of claim 11, wherein the executable modules comprise:
a determining sub-module configured to determine related information of the head movement according to the electrooculographic information and the piece of reference information; and
an executing sub-module configured to execute the operation according to the related information.

13. The wearable smart glass device of claim 12, wherein the determining sub-module comprises:
a type determining unit configured to determine a type of the head movement according to the electrooculographic information and the piece of reference information.

14. The wearable smart glass device of claim 13, wherein the type determining unit comprises:
a target waveform determining sub-unit configured to determine a target waveform in the electrooculographic information; and
a type determining sub-unit configured to determine the type of the head movement according to the target waveform and a reference waveform.

15. The wearable smart glass device of claim 14, wherein the type determining sub-unit is configured to cross-correlate the target waveform and the reference waveform, separately, and determine the type of the head movement according to a computed result by the type determining sub-unit.

16. The wearable smart glass device of claim 13, wherein the type determining unit comprises:
a target signal characteristic determining sub-unit configured to determine a target signal characteristic in the electrooculographic information; and
a type determining sub-unit configured to determine the type of the head movement according to the target signal characteristic and a reference signal characteristic.

17. The wearable smart glass device of claim 13, wherein the head movement comprises a first type head movement, the piece of reference information comprises first reference information corresponding to the first type head movement, and
the determining sub-module further comprises:
a number of times determining unit configured to determine a number of the first type head movements according to the electrooculographic information and the first reference information.

18. The wearable smart glass device of claim 17, wherein the number of times determining unit comprises:
a target waveform determining sub-unit configured to determine a target waveform in the electrooculographic information; and
a number of times determining sub-unit configured to determine the number of the first type head movements according to a quantity of first reference waveforms comprised in the target waveform.

19. The wearable smart glass device of claim 17, wherein the number of times determining unit comprises:
a target signal characteristic determining sub-unit configured to determine a target signal characteristic in the electrooculographic information; and
a number of times determining sub-unit configured to determine the number of the first type head movements according to a quantity of first reference signal characteristics comprised in the target signal characteristic.

20. The wearable smart glass device of claim 11, wherein a wearable equipment comprises the apparatus.

21. A wearable smart glass device, comprising at least one executable instruction, which, in response to execution, causes the wearable smart glass device comprising a processor to perform operations, comprising:
acquiring, in response to a head movement of a user, electrooculographic information of the user; and
executing an operation corresponding to the head movement according to the electrooculographic information and at least one piece of reference information.

22. A wearable smart glass device, characterized by comprising a processor and a memory, the memory storing executable instructions, the processor being connected to the memory through a communication bus, and when the wearable smart glass device operates, the processor executing the executable instructions stored in the memory, so that the wearable smart glass device executes operations, comprising:
in response to determining that a head movement has occurred associated with a user identity, acquiring electrooculographic information of the user identity; and
executing an operation corresponding to the head movement based at least on the electrooculographic information and reference information that facilitates an interpretation of the electrooculographic information.

* * * * *